United States Patent
Molz

(10) Patent No.: US 8,075,596 B2
(45) Date of Patent: Dec. 13, 2011

(54) SPINAL PROSTHESIS SYSTEMS

(75) Inventor: Fred J. Molz, Birmingham, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 810 days.

(21) Appl. No.: 11/622,778

(22) Filed: Jan. 12, 2007

(65) Prior Publication Data

US 2008/0172090 A1  Jul. 17, 2008

(51) Int. Cl.
*A61B 17/70* (2006.01)
(52) U.S. Cl. .................... 606/257; 623/17.14
(58) Field of Classification Search ............. 623/17.11, 623/17.14, 17.15–17.17
See application file for complete search history.

(56) References Cited

U.S. PATENT DOCUMENTS

| | | |
|---|---|---|
| 4,349,921 A | 9/1982 | Kuntz |
| 4,697,582 A | 10/1987 | Williams |
| 5,092,866 A | 3/1992 | Breard et al. |
| 5,258,031 A | 11/1993 | Salib et al. |
| 5,282,863 A | 2/1994 | Burton |
| 5,387,213 A | 2/1995 | Breard et al. |
| 5,401,269 A | 3/1995 | Buttner-Janz et al. |
| 5,415,661 A | 5/1995 | Holmes |
| 5,507,816 A | 4/1996 | Bullivant |
| 5,553,431 A | 9/1996 | Buttner-Janz |
| 5,562,660 A | 10/1996 | Grob |
| 5,562,737 A | 10/1996 | Graf |
| 5,562,738 A * | 10/1996 | Boyd et al. ............... 623/17.15 |
| 5,672,175 A | 9/1997 | Martin |
| 5,676,701 A | 10/1997 | Yuan et al. |
| 5,702,450 A | 12/1997 | Bisserie |
| 5,895,428 A | 4/1999 | Berry |
| 5,899,941 A | 5/1999 | Nishijima et al. |
| RE36,221 E | 6/1999 | Breard et al. |
| 5,961,516 A | 10/1999 | Graf |
| 6,039,763 A * | 3/2000 | Shelokov ............... 623/17.16 |
| RE36,758 E | 6/2000 | Fitz |
| 6,113,637 A | 9/2000 | Gill |
| 6,132,464 A | 10/2000 | Martin |
| 6,146,421 A | 11/2000 | Gordon et al. |
| 6,156,067 A | 12/2000 | Bryan et al. |

(Continued)

FOREIGN PATENT DOCUMENTS

DE  10135771 A1  2/2003

(Continued)

OTHER PUBLICATIONS

Yu et al, Instrument and Methods for Preparing an Interverbral Space, U.S. Appl. No. 11/393,488 dated Mar. 30, 2006.

(Continued)

*Primary Examiner* — Todd Manahan
*Assistant Examiner* — Lynnsy Schneider

(57) ABSTRACT

A spinal prosthesis system includes: an anterior portion having an upper component and a lower component, the upper and lower components capable of relative movement about a first point; a posterior portion separate from the anterior portion, the posterior portion having an upper portion and a lower portion, the upper and lower portions capable of relative movement concentric to the upper and lower components about the first point. In another form, a method includes: determining a motion profile of a vertebral motion segment; determining a point of rotation based upon the motion profile; and manufacturing a spinal stabilization system having an anterior portion and a posterior portion, the anterior and posterior portions each having a center of rotation located at the point of rotation.

27 Claims, 8 Drawing Sheets

U.S. PATENT DOCUMENTS

| | | |
|---|---|---|
| 6,179,874 B1 | 1/2001 | Cauthen |
| 6,179,875 B1 | 1/2001 | Strempel |
| 6,228,118 B1 | 5/2001 | Gordon |
| 6,368,350 B1 | 4/2002 | Erickson et al. |
| 6,402,750 B1 | 6/2002 | Atkinson et al. |
| 6,419,703 B1 | 7/2002 | Fallin et al. |
| 6,517,580 B1 | 2/2003 | Ramadan et al. |
| 6,527,804 B1 | 3/2003 | Gauchet et al. |
| 6,540,747 B1 | 4/2003 | Marino |
| 6,540,785 B1 | 4/2003 | Gill et al. |
| 6,565,571 B1 | 5/2003 | Jackowski et al. |
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,486 B1 | 6/2003 | Gauchet |
| 6,610,091 B1 | 8/2003 | Reiley |
| 6,610,093 B1 | 8/2003 | Pisharodi |
| 6,669,729 B2 | 12/2003 | Chin |
| 6,679,915 B1 | 1/2004 | Cauthen |
| 6,692,495 B1 | 2/2004 | Zacouto |
| 6,811,567 B2 | 11/2004 | Reiley |
| 6,835,205 B2 | 12/2004 | Atkinson et al. |
| 6,949,123 B2 | 9/2005 | Reiley |
| 6,994,727 B2 | 2/2006 | Khandkar et al. |
| 7,022,138 B2 | 4/2006 | Mashburn |
| 7,041,136 B2 | 5/2006 | Goble et al. |
| 7,052,515 B2 | 5/2006 | Simonson |
| 7,066,957 B2 | 6/2006 | Graf |
| 7,074,237 B2 | 7/2006 | Goble et al. |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,599 B2* | 10/2006 | Errico et al. ............... 623/17.14 |
| 7,204,853 B2 | 4/2007 | Gordon et al. |
| 7,491,180 B2* | 2/2009 | Pacheco ........................ 600/594 |
| 2002/0095154 A1 | 7/2002 | Atkinson et al. |
| 2002/0123806 A1 | 9/2002 | Reiley |
| 2002/0133155 A1 | 9/2002 | Ferree |
| 2002/0151895 A1 | 10/2002 | Soboleski et al. |
| 2003/0004572 A1 | 1/2003 | Goble et al. |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0139812 A1 | 7/2003 | Garcia et al. |
| 2003/0139813 A1 | 7/2003 | Messerli et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204271 A1 | 10/2003 | Ferree |
| 2003/0233146 A1 | 12/2003 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0138749 A1 | 7/2004 | Zucherman et al. |
| 2004/0181284 A1 | 9/2004 | Simonson |
| 2004/0181285 A1 | 9/2004 | Simonson |
| 2004/0225289 A1 | 11/2004 | Biedermann et al. |
| 2004/0243239 A1 | 12/2004 | Taylor |
| 2005/0021031 A1 | 1/2005 | Foley et al. |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0049708 A1 | 3/2005 | Atkinson et al. |
| 2005/0112835 A1 | 3/2005 | Serhan et al. |
| 2005/0080486 A1 | 4/2005 | Fallin et al. |
| 2005/0102028 A1 | 5/2005 | Arnin et al. |
| 2005/0113927 A1 | 5/2005 | Malek |
| 2005/0131405 A1 | 6/2005 | Molz et al. |
| 2005/0131538 A1* | 6/2005 | Chervitz et al. ............ 623/17.11 |
| 2005/0143820 A1 | 6/2005 | Zucherman et al. |
| 2005/0149196 A1 | 7/2005 | Zucherman et al. |
| 2005/0154390 A1 | 7/2005 | Biedermann et al. |
| 2005/0154462 A1 | 7/2005 | Zucherman et al. |
| 2005/0154464 A1 | 7/2005 | Humphreys et al. |
| 2005/0154465 A1 | 7/2005 | Peterman et al. |
| 2005/0154466 A1 | 7/2005 | Eisermann et al. |
| 2005/0154467 A1 | 7/2005 | Peterman et al. |
| 2005/0154461 A1 | 8/2005 | Peterman et al. |
| 2005/0171608 A1 | 8/2005 | Peterman et al. |
| 2005/0171609 A1 | 8/2005 | Humphreys et al. |
| 2005/0171610 A1 | 8/2005 | Eisermann et al. |
| 2005/0119642 A1 | 9/2005 | Zucherman et al. |
| 2005/0192671 A1 | 9/2005 | Bao et al. |
| 2005/0203624 A1 | 9/2005 | Serhan et al. |
| 2005/0209603 A1 | 9/2005 | Zucherman et al. |
| 2005/0216005 A1* | 9/2005 | Howland ........................ 606/61 |
| 2005/0234551 A1 | 10/2005 | Fallin et al. |
| 2005/0234552 A1 | 10/2005 | Reiley |
| 2005/0234555 A1 | 10/2005 | Sutton et al. |
| 2005/0240270 A1 | 10/2005 | Zubok et al. |
| 2005/0256578 A1 | 11/2005 | Blatt et al. |
| 2005/0261773 A1 | 11/2005 | Ferree |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0277930 A1 | 12/2005 | Parsons |
| 2005/0277938 A1 | 12/2005 | Parsons |
| 2005/0278026 A1 | 12/2005 | Gordon et al. |
| 2005/0283237 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0004448 A1 | 1/2006 | Casey |
| 2006/0004449 A1 | 1/2006 | Goble et al. |
| 2006/0004451 A1 | 1/2006 | Goble et al. |
| 2006/0009849 A1 | 1/2006 | Reiley |
| 2006/0036325 A1 | 2/2006 | Paul et al. |
| 2006/0069438 A1 | 3/2006 | Zucherman et al. |
| 2006/0069440 A1 | 3/2006 | Zucherman et al. |
| 2006/0079896 A1 | 4/2006 | Kwak et al. |
| 2006/0084976 A1 | 4/2006 | Borgstrom et al. |
| 2006/0084991 A1 | 4/2006 | Borgstrom et al. |
| 2006/0084994 A1 | 4/2006 | Atkinson et al. |
| 2006/0085076 A1* | 4/2006 | Krishna et al. ............. 623/17.15 |
| 2006/0089717 A1* | 4/2006 | Krishna et al. ............. 623/17.11 |
| 2006/0111782 A1 | 5/2006 | Petersen |
| 2006/0149229 A1 | 7/2006 | Kwak et al. |
| 2006/0149230 A1 | 7/2006 | Kwak et al. |
| 2006/0149383 A1 | 7/2006 | Arnin et al. |
| 2006/0178745 A1 | 8/2006 | Bartish, Jr. et al. |
| 2006/0195192 A1 | 8/2006 | Gordon et al. |
| 2006/0241642 A1 | 10/2006 | Arnin et al. |
| 2006/0241769 A1 | 10/2006 | Gordon et al. |
| 2006/0241771 A1* | 10/2006 | Gordon et al. ............. 623/17.15 |
| 2006/0247635 A1 | 11/2006 | Gordon et al. |
| 2006/0247779 A1* | 11/2006 | Gordon et al. ............. 623/17.15 |
| 2006/0265069 A1 | 11/2006 | Goble et al. |
| 2006/0265074 A1* | 11/2006 | Krishna et al. ............. 623/17.15 |
| 2006/0271046 A1 | 11/2006 | Kwak et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2007/0073396 A1 | 3/2007 | Arnin |
| 2007/0073405 A1 | 3/2007 | Verhulst et al. |
| 2007/0073406 A1 | 3/2007 | Gordon et al. |
| 2007/0083200 A1 | 4/2007 | Gittings et al. |

| | | | |
|---|---|---|---|
| 2007/0168039 | A1 | 7/2007 | Trieu |
| 2007/0173820 | A1 | 7/2007 | Trieu |
| 2007/0173821 | A1 | 7/2007 | Trieu |
| 2007/0173822 | A1 | 7/2007 | Anderson et al. |
| 2007/0179616 | A1 | 8/2007 | Braddock et al. |
| 2007/0191945 | A1 | 8/2007 | Yu et al. |
| 2007/0288094 | A1* | 12/2007 | Krishna et al. ............. 623/17.15 |
| 2008/0015585 | A1* | 1/2008 | Berg et al. ....................... 606/61 |
| 2008/0077137 | A1* | 3/2008 | Balderston ..................... 606/61 |
| 2008/0161921 | A1* | 7/2008 | Carls et al. ................ 623/17.11 |

FOREIGN PATENT DOCUMENTS

| | | |
|---|---|---|
| DE | 202004015198 A1 | 11/2004 |
| EP | 0677277 A2 | 10/1995 |
| EP | 1281361 A1 | 2/2003 |
| FR | 2676911 A1 | 12/1992 |
| FR | 2799638 A1 | 4/2001 |
| WO | 9600049 A1 | 1/1996 |
| WO | 9953871 A1 | 10/1999 |
| WO | 0004851 A1 | 2/2000 |
| WO | 0139678 A1 | 6/2001 |
| WO | 0145576 A1 | 6/2001 |
| WO | 0247586 A1 | 6/2002 |
| WO | 03041618 A2 | 5/2003 |
| WO | 03045262 A2 | 6/2003 |
| WO | 03084449 A1 | 10/2003 |
| WO | 03101350 A1 | 12/2003 |
| WO | 2004034935 A1 | 4/2004 |
| WO | 2004041131 A2 | 5/2004 |
| WO | 2004098465 A1 | 11/2004 |
| WO | WO2004098466 A2 | 11/2004 |
| WO | 2005112835 A2 | 12/2005 |
| WO | WO2007142744 A | 12/2007 |

OTHER PUBLICATIONS

Yu et al, Prosthetic Device for Spinal Joint Reconstruction, U.S. Appl. No. 11/494,311 dated Jul. 27, 2006.

Carls et al, Posterior Total Joint Replacement, U.S. Appl. No. 11/757,084 dated Jun. 1, 2007.

European Patent Office, International Searching Authority, Notification of Transmittal of the International Search Report and the Written Opinion of the International Searching Authority or the Declaration, International Application No. PCT/US2005/000648, Jun. 6, 2005, 9 pages.

European Patent Office, International Searching Authority, Notification of Transmittal of the International Search Report and the Written Opinion of the International Searching Authority or the Declaration, International Application No. PCT/US2005/000705, Jun. 6, 2005, 11 pages.

European Patent Office, International Searching Authority, Notification of Transmittal of the International Search Report and the Written Opinion of the International Searching Authority or the Declaration, International Application No. PCT/US2005/000585, Jun. 8, 2005, 9 pages.

European Patent Office, International Searching Authority, Notification of Transmittal of the International Search Report and the Written Opinion of the International Searching Authority or the Declaration, International Application No. PCT/US2005/000656, Aug. 23, 2005, 8 pages.

European Patent Office, International Searching Authority, Notification of Transmittal of the International Search Report and the Written Opinion of the International Searching Authority or the Declaration, International Application No. PCT/US2005/000704, Aug. 23, 2005, 13 pages.

European Patent Office, International Searching Authority, Notification of Transmittal of the International Search Report and the Written Opinion of the International Searching Authority or the Declaration, International Application No. PCT/US2005/000586, Dec. 16, 2005, 8 pages.

Search Report for PCT/US2008/050592, Jul. 2, 2008.

* cited by examiner

SPINAL PROSTHESIS SYSTEMS

TECHNICAL FIELD

Embodiments of the present disclosure relate generally to devices and methods for accomplishing spinal surgery, and more particularly in some embodiments, to devices and methods relating to spinal prosthesis systems having anterior and posterior portions with a concentric (i.e., same) center of rotation.

BACKGROUND

Spinal implants are often comprised of multiple components. For example, some spinal implants include anterior and posterior portions that are each configured to preserve at least some vertebral motion. However, the anterior and posterior portions can adversely affect each other during motion by placing undesirable loads on the opposing portion. Although existing devices and methods have been generally adequate for their intended purposes, they have not been entirely satisfactory in all respects.

SUMMARY

In one embodiment, a spinal prosthesis having a motion-preserving anterior portion and a motion-preserving posterior portion is provided. The anterior and posterior portions function so as not to adversely affect one another during motion.

In a second embodiment, a spinal prosthesis having a motion-preserving anterior portion and a motion-preserving posterior portion is provided wherein the anterior and posterior portions have concentric centers of rotation.

In another embodiment, a method of inserting a spinal prosthesis having a motion-preserving anterior portion and a motion-preserving posterior portion with concentric centers of rotation is provided Additional and alternative features, advantages, uses, and embodiments are set forth in or will be apparent from the following description, drawings, and claims.

DESCRIPTION

Figure 1:
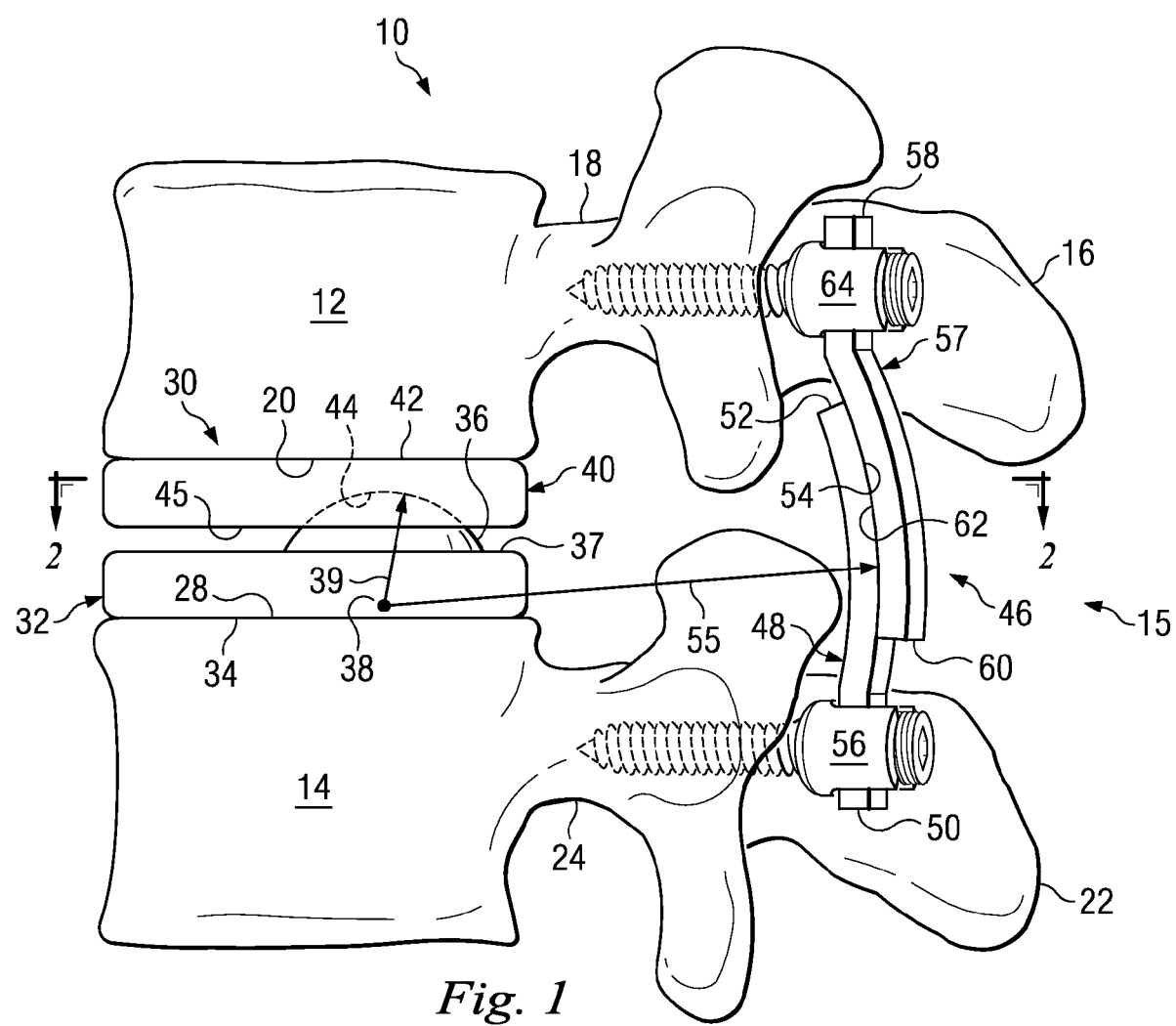
FIG. 1 is a diagrammatic side view of an arrangement that embodies aspects of the present disclosure.

For the purposes of promoting an understanding of the principles of the invention, reference will now be made to the embodiments, or examples, illustrated in the drawings and specific language will be used to describe the embodiments. It will nevertheless be understood that no limitation of the scope of the invention is intended. Any alterations and further modifications of the described embodiments, and any further applications of the principles of the invention as described herein are contemplated as would normally occur to one skilled in the art to which the invention relates.

Figure 2A:
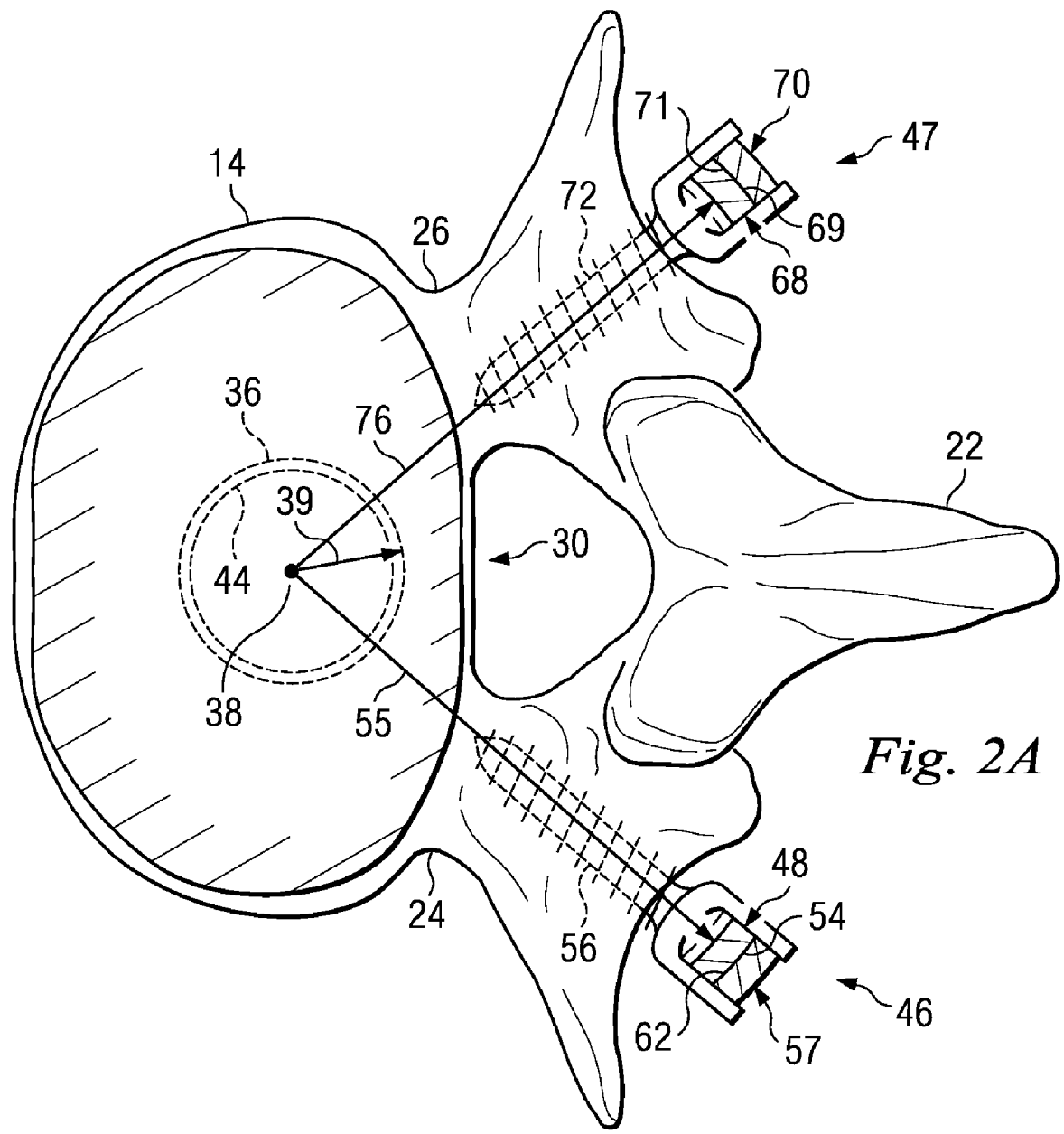
FIG. 2A is a sectional view of the arrangement of FIG. 1 taken along section line 2-2.
Figure 3:
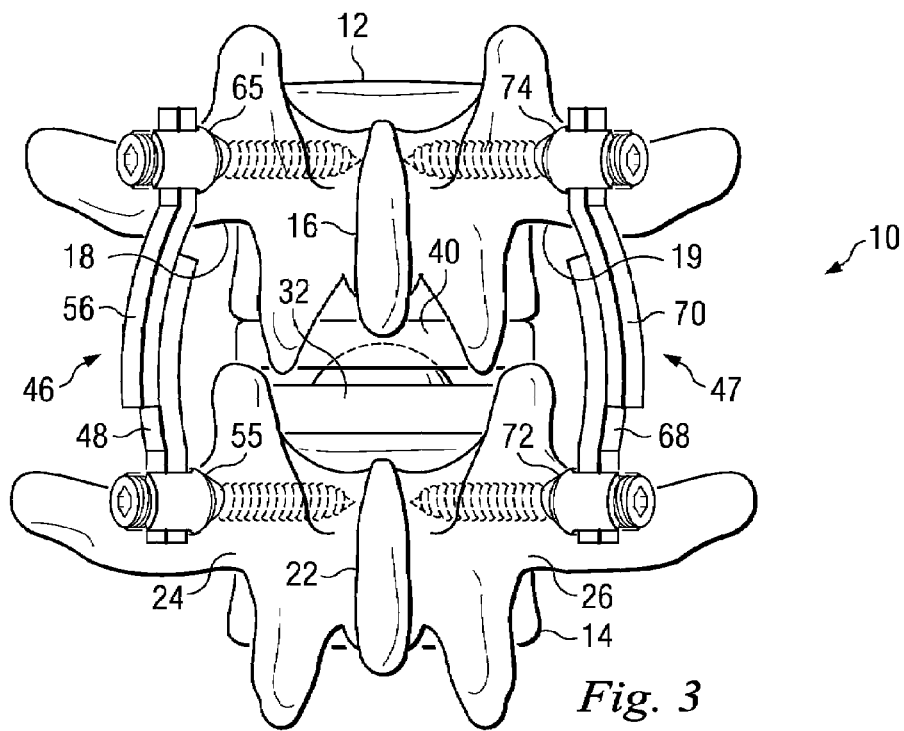
FIG. 3 is diagrammatic posterior view of the arrangement of FIG. 1.

FIG. 1 is a diagrammatic side view of an arrangement 10 that embodies aspects of the present invention. The arrangement 10 includes a vertebra 12, a vertebra 14, and an apparatus 15. FIG. 2A is a sectional view of the arrangement 10 of FIG. 1 taken along section line 2-2. FIG. 3 is diagrammatic posterior view of the arrangement 10 of FIG. 1.

Referring to FIGS. 1-3, the vertebra 12 includes a spinous process 16, a left pedicle 18, a right pedicle 19, and an inferior endplate 20. Similarly, the vertebra 14 includes a spinous process 22, a left pedicle 24, a right pedicle 26, and a superior endplate 28.

The apparatus 15 is a prosthesis system adapted to preserve at least some motion between the vertebrae 12 and 14. The apparatus 15 includes an anterior portion 30. The anterior portion 30 includes an inferior piece 32. The inferior piece 32 includes an inferior surface 34 that is adapted to engage with the superior endplate 28 of vertebra 14. The inferior surface 34 may include features adapted to enhance engagement with the endplate 28, including projections, such as spikes, keels, ridges, or other surface textures; surface treatments, such as chemical etching, bead-blasting, sanding, grinding, serrating, diamond-cutting, coating with a biocompatible and osteoconductive material (such as hydroxyapatite (HA), tricalcium phosphate (TCP), or calcium carbonate), or coating with osteoinductive materials (such as proteins from the transforming growth factor (TGF) beta superfamily or bone-morphogenic proteins, such as BMP2 or BMP7); or other features. The inferior piece 32 also includes a projection 36. The projection 36 extends out of a superior surface 37 of the inferior piece 32. The projection 36 is curved to substantially coincide with a virtual sphere centered about a center point 38 with a radius 39. As shown in FIG. 1, the projection 36 is positioned posteriorly from a central portion of the inferior piece 32 in the anterior/posterior direction. As shown in FIG. 2A, however, the projection 36 is centered about the central portion of the inferior piece 32 in the lateral direction.

The anterior portion 30 also includes a superior piece 40. The superior piece 40 includes a superior surface 42 that is adapted to engage with the inferior endplate 20 of vertebra 12. Similar to inferior surface 34 of the inferior piece 32, the superior surface 42 may include features adapted to enhance engagement with the endplate 20. The superior piece 40 also includes a recess 44. The recess 44 extends into an inferior surface 45 of the superior piece 40. The recess 44 is adapted to movably mate with the projection 36 of the inferior piece 32. Thus, the recess 44 is substantially spherical about the center point 38 to match the projection 36. However, when mated together the recess 44 does not fully envelope the projection 36, leaving space between the pieces 32 and 40, to allow for spherical, rotational movement about the center point 38 between the inferior piece 32 and the superior piece 40. Thus, the anterior portion 30 of the apparatus 15 provides load-bearing support to the anterior portion of the vertebral joint while still allowing some movement to help preserve motion between the vertebrae 12 and 14. In some embodiments the anterior portion 30 can be a Prestige cervical disc available from Medtronic, Inc. In some embodiments, the anterior portion 30 can be a Maverick lumbar disc also available from Medtronic, Inc.

The apparatus also includes two posterior portions 46 and 47 (FIGS. 2 and 3). The posterior portion 46 includes an inferior part 48. The inferior part 48 includes a lower section 50 and an upper section 52. A surface 54 extends at least partially between the lower section 50 and the upper section 52 on the posterior side of the inferior part 48. As shown, the surface 54 is curved to substantially coincide with a virtual sphere centered about center point 38 with a radius 55. Thus, the surface 54 is curved in both the vertical plane (best seen in FIG. 1) and the horizontal plane (best seen in FIG. 2A).

The inferior part 48 is secured to pedicle 24 of vertebra 14 by a mechanism 56. The mechanism 56 receives a portion of the lower section 50 of the inferior part 48. The mechanism 56 includes a screw portion adapted to engage and extend into the pedicle 24. In some embodiments, the inferior part 48 includes an opening adapted to receive a pedicle screw directly. Further, in some embodiments the inferior part 48 may be secured to the pedicle 24 using appropriate means other than a pedicle screw.

The posterior portion 46 also includes a superior part 57. The superior part 57 includes an upper section 58 and a lower section 60. A surface 62 extends at least partially between the upper section 58 and the lower section 60 on the anterior side of the superior part 57. The surface 62 is curved to movably mate with the surface 54 of the inferior part 48. Similar to the surface 54, the surface 62 is curved to substantially coincide with the virtual sphere centered about center point 38 with radius 55. Thus, the surface 62 is also curved in both the vertical plane (best seen in FIG. 1) and the horizontal plane (best seen in FIG. 2A).

The superior part 57 is secured to pedicle 18 of vertebra 12 by a mechanism 64. The mechanism 64 receives a portion of the upper section 58 of the superior part 57. The mechanism 64 includes a screw portion adapted to engage and extend into the pedicle 24. In some embodiments, the superior part 57 includes an opening adapted to receive a pedicle screw directly. Further, in some embodiments the superior part 57 may be secured to the pedicle 18 using appropriate means other than a pedicle screw.

The surfaces 54 and 62 movably mate to allow for spherical, rotational movement about the center point 38 between the inferior part 48 and the superior part 57. In this manner, the posterior portion 46 of the apparatus 15 provides load-bearing support to the posterior portion of the vertebral joint while still allowing some movement to help preserve motion between the vertebrae 12 and 14.

Thus, the anterior portion 30 and the posterior portion 46 allow for movement about the same center of rotation, namely center point 38. Therefore, the anterior portion 30 will not adversely load or affect the posterior portion 46 during movement between the inferior and superior pieces 32 and 40. Similarly, the posterior portion 46 will not adversely load or affect the anterior portion 30 during movement between the inferior part 48 and superior part 57. Thus, the anterior portion 30 and posterior portion 46 of the apparatus 15 function together to provide load-bearing support and preserve vertebral motion between the vertebrae 12 and 14 without adversely affecting each other.

Figure 2B:
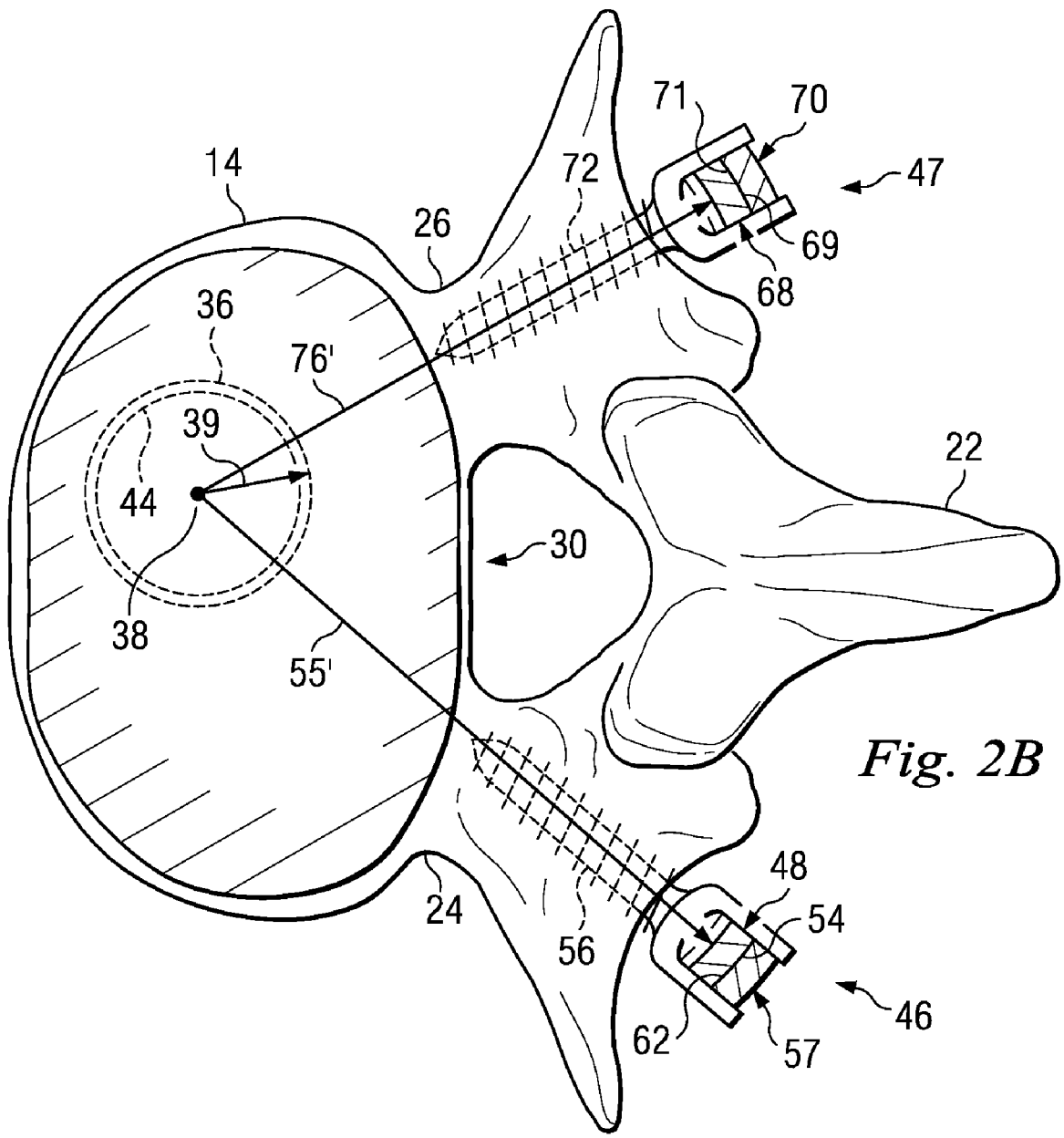
FIG. 2B is a sectional view of an arrangement similar to FIG. 2A, but showing an alternative embodiment.

Referring more specifically to FIGS. 2 and 3, in the current embodiment the posterior portion 47 is substantially similar to posterior portion 46 described above and, therefore, various aspects will not be described in great detail. The posterior portion 47 includes an inferior part 68 with a surface 69 and a superior part 70 with a surface 71. The inferior part 68 is secured to the pedicle 26 of vertebra 14 by mechanism 72. The superior part 70 is secured to the pedicle 19 of the vertebra 12 by mechanism 74. The surfaces 69 and 71 are curved to substantially coincide with a virtual sphere centered about center point 38 with a radius 76. The radius 76 has substantially the same length as radius 55 for posterior portion 46. Thus, the surfaces 69 and 71 are defined by the same virtual sphere that defines surfaces 54 and 62. However, in other embodiments the radii of the posterior portions 46 and 47 may have different lengths, such that the surfaces of posterior portion 47 are not defined by the same virtual sphere as the surfaces of posterior portion 46, but the posterior devices maintain the same center point. For example, as shown in FIG. 2B, a radius 55' of posterior portion 46 can be greater than a radius 76' of posterior portion 47. In other embodiments, the radius 55' can be less than the radius 76'. In some embodiments, the difference in length is a result of non-symmetrical physical attributes of the patient. In other embodiments, the difference in length is a result of the center of rotation being off-center with respect to the vertebrae (as shown in FIG. 2B).

Figure 2C:
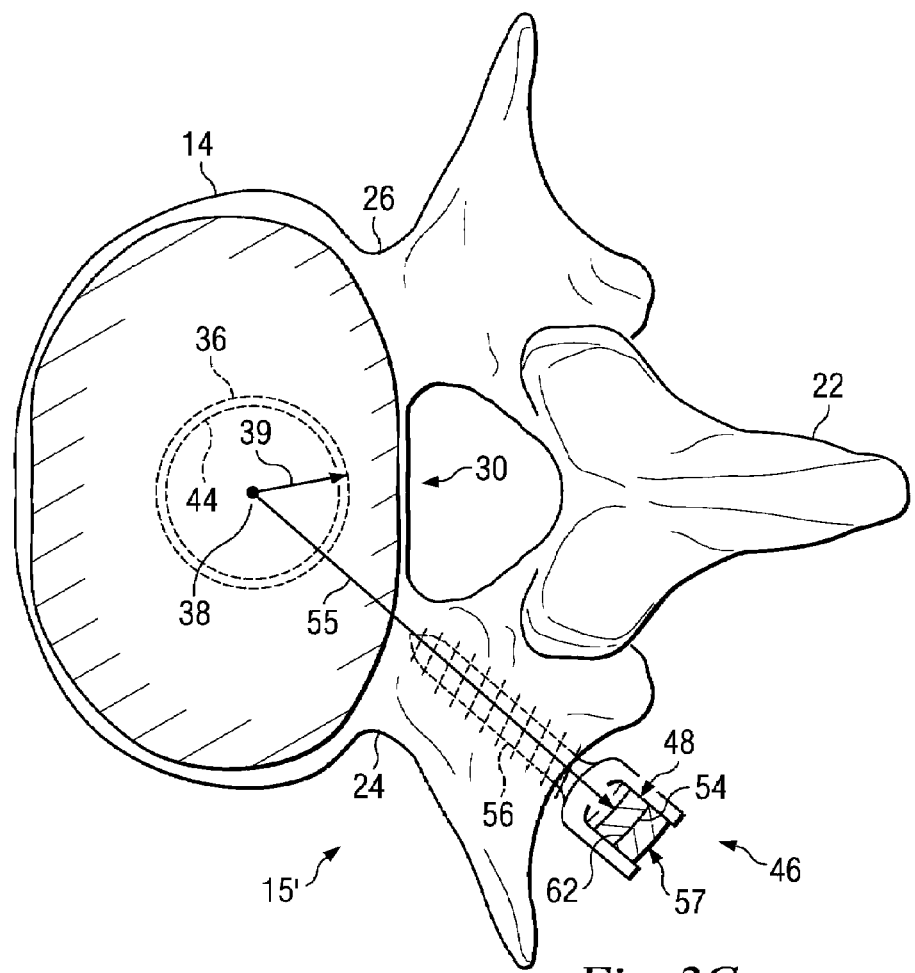
FIG. 2C is a sectional view of arrangement similar to FIG. 2A, but showing an alternative embodiment.

The surfaces 69 and 71 movably mate to allow for spherical, rotational movement about the center point 38 between the inferior part 68 and the superior part 70. In this manner, the posterior portion 47 of the apparatus 15 provides load-bearing support to the posterior portion of the vertebral joint while still allowing some movement to help preserve motion between the vertebrae 12 and 14. Thus, the anterior portion 30, the posterior portion 46, and the posterior portion 47 allow for movement about the same center of rotation, namely center point 38. Thus, the anterior portion 30 will not adversely load or adversely affect the posterior portion 47 during movement, and vice-versa. Similarly, the posterior portion 46 will not adversely load or affect the posterior portion 47 during movement, and vice-versa. Thus, the anterior portion 30 and the posterior portions 46 and 47 of the apparatus 15 function together to provide load-bearing support and preserve vertebral motion between the vertebrae 12 and 14 without adversely affecting one another. In other embodiments, the apparatus 15 may be a unilateral rather than a bilateral. That is, in some embodiments the apparatus 15 includes only a single posterior portion. For example, as shown in FIG. 2C, an apparatus 15' includes the anterior portion 30 and the posterior portion 46. Though currently illustrated as being positioned on the left side of the vertebrae, in other embodiments the posterior portion 46 is positioned on the right side.

Figure 4:
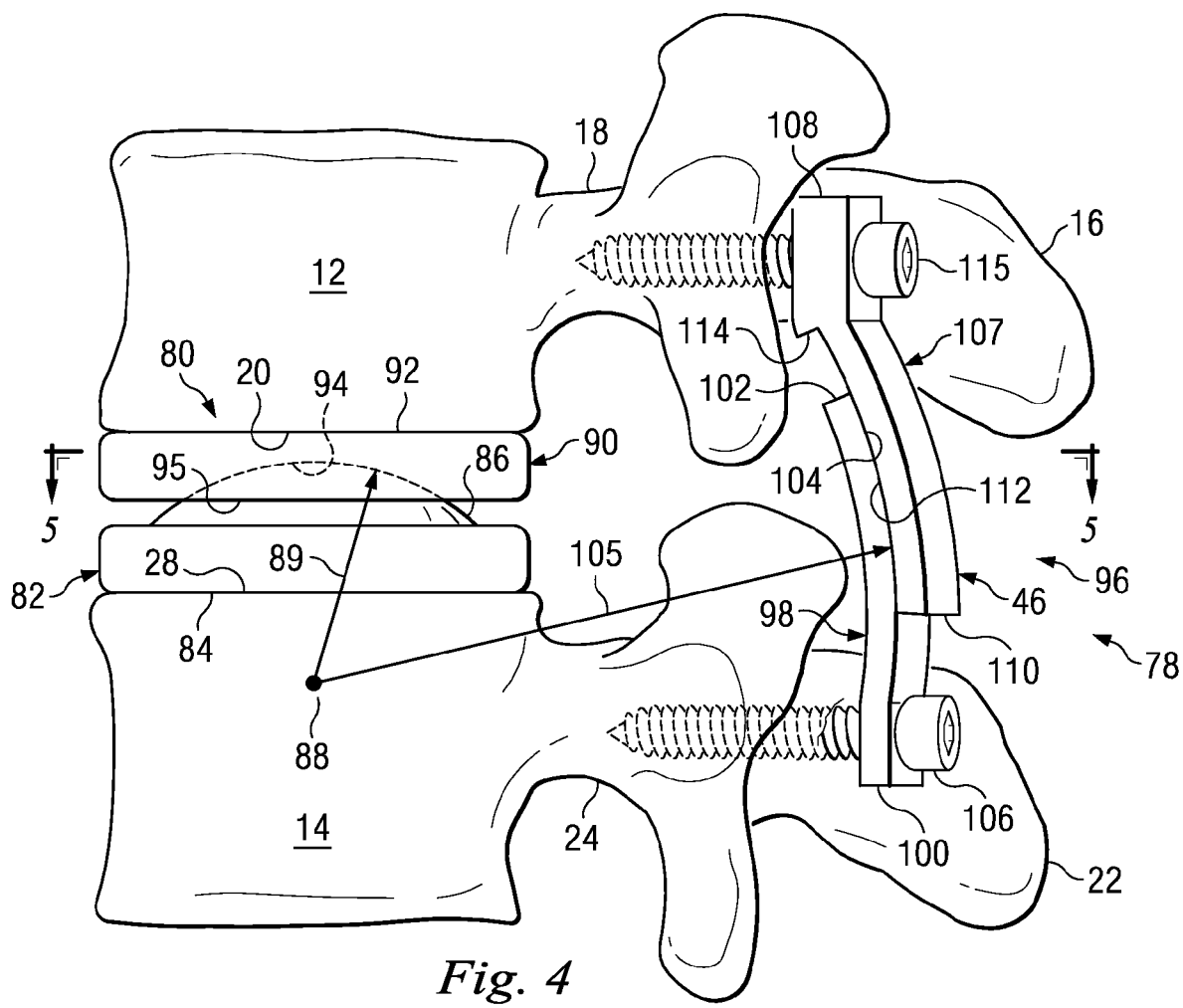
FIG. 4 is a diagrammatic side view similar to FIG. 1, but showing an alternative embodiment.
Figure 5:
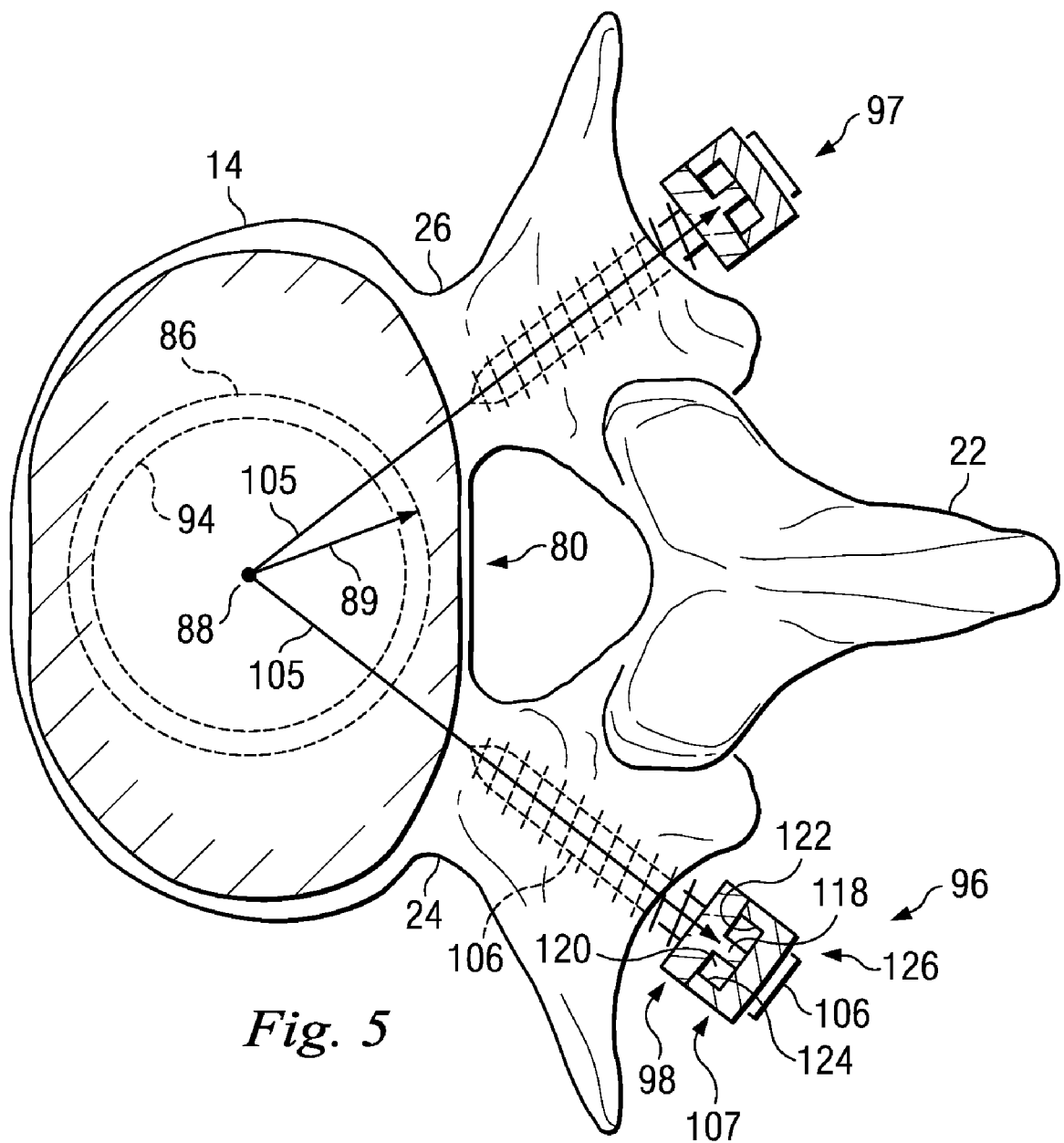
FIG. 5 is a sectional view of the arrangement of FIG. 4 taken along section line 5-5.

FIG. 4 is a diagrammatic side view similar to FIG. 1, but showing an apparatus 78 that is an alternative embodiment of the apparatus 15 described above. Apparatus 78 is similar to apparatus 15 in many respects and, therefore, some aspects will not be described in great detail. FIG. 5 is a sectional view of FIG. 4 taken along section line 5-5.

The apparatus 78 is a prosthesis system adapted to preserve at least some motion between the vertebrae 12 and 14. The apparatus 78 includes an anterior portion 80. The anterior portion 80 includes an inferior piece 82. The inferior piece 82 includes an inferior surface 84 that is adapted to engage with the superior endplate 28 of vertebra 14. The inferior surface 84 may include features adapted to enhance engagement with the endplate 28. The inferior piece 82 also includes a projection 86. The projection 86 extends out of a superior surface 87 of the inferior piece 82. The projection 86 is curved to substantially coincide with a virtual sphere centered about a center point 88 with a radius 89. In this embodiment, the projection 86 is centered about a central portion of the inferior piece 82 in both the anterior/posterior and lateral directions.

The anterior portion 80 also includes a superior piece 90. The superior piece 90 includes a superior surface 92 that is adapted to engage with the inferior endplate 20 of vertebra 12.

Similar to inferior surface 84 of the inferior piece 82, the superior surface 92 may include features adapted to enhance engagement with the endplate 28. The superior piece 90 also includes a recess 94. The recess 94 extends into an inferior surface 95 of the superior piece 90. The recess 94 is adapted to movably mate with the projection 86 of the inferior piece 82. Thus, the recess 94 is substantially spherical about the center point 88 to match the projection 86. However, when mated together the recess 94 does not fully envelope the projection 86, leaving space between the pieces 82 and 90, to allow for spherical, rotational movement about the center point 88. In this manner, the anterior portion 80 of the apparatus 78 provides load-bearing support to the anterior portion of the vertebral joint while still allowing some movement to help preserve motion between the vertebrae 12 and 14.

The apparatus 78 also includes two posterior portions 96 and 97. The posterior portion 96 is seen in FIGS. 4 and 5. The posterior portion 97 is only presented in a partial, sectional view in FIG. 5. In the current embodiment the posterior portion 97 is substantially similar to posterior portion 96 and, therefore, will not be described in detail. The posterior portion 96 includes an inferior part 98. The inferior part 98 includes a lower section 100 and an upper section 102. A surface 104 extends at least partially between the lower section 100 and the upper section 102 on the posterior side of the inferior part 98. As shown, the surface 104 is curved to substantially coincide with a virtual sphere centered about center point 88 with a radius 105. Thus, the surface 104 is curved in both the vertical plane (best seen in FIG. 4) and the horizontal plane (best seen in FIG. 5). The inferior part 98 is secured to pedicle 24 of vertebra 14 by a pedicle screw 106. The pedicle screw 106 sized to pass through an opening in the lower section 100 of the inferior part 98 and into the pedicle 24. In other embodiments the inferior part 98 is secured to the pedicle 24 using means other than a pedicle screw.

The posterior portion 96 also includes a superior part 107. The superior part 107 includes an upper section 108 and a lower section 110. A surface 112 extends at least partially between the upper section 108 and the lower section 110 on the anterior side of the superior part 107. The surface 112 is curved to movably mate with the surface 104 of the inferior part 98. Similar to the surface 104, the surface 112 is curved to substantially coincide with the virtual sphere centered about center point 88 with radius 105. Thus, the surface 112 is also curved in both the vertical plane (best seen in FIG. 4) and the horizontal plane (best seen in FIG. 5). The surface 112 is bounded on the upper end by a stop portion 114. The stop portion 114 extends anteriorly from surface 112 and, as described in more detail below, serves to limit the range of motion allowed by the posterior portion 96 of the apparatus 78. The superior part 107 is secured to pedicle 18 of vertebra 12 by a pedicle screw 115. The pedicle screw 115 is sized to pass through an opening in the upper section 108 of the superior part 107 and into the pedicle 18. In other embodiments the superior part 107 is secured to the pedicle 18 using means other than a pedicle screw.

The surfaces 104 and 112 movably mate to allow for spherical, rotational movement about the center point 88 between the inferior part 98 and the superior part 107. In this manner, the posterior portion 96 of the apparatus 78 provides load-bearing support to the posterior portion of the vertebral joint while still allowing some movement to help preserve motion between the vertebrae 12 and 14. However, the degree of spherical, rotational movement allowed in extension is limited by stop portion 114. As the motion segment moves further into extension, the upper section 102 of the lower part 98 moves closer and closer to the stop portion 114 until they make contact. The contact between the upper section 102 and the stop portion 114 serves as a hard stop to limit the degree of extension allowed by the posterior portion 96. The amount of extension allowed can be tailored for the condition of the specific patient.

Further, as best seen in FIG. 5, the lower part 98 includes a projection 118 adapted to slot in a recess 120 in the upper part 107. The recess 120 is bounded laterally by stop portions 122 and 124. There is space between the projection 118 and stop portions 122 and 124 to allow left and right rotational movement of the spine. However, the degree of rotational movement is limited by the stop portions. As the motion segment rotates, the projection 118 of the lower part 98 moves closer and closer to the stop portions 122 (in left rotation) and 124 (in right rotation) until they make contact. The contact between the upper section 102 and the stop portions 122 and 124 serves as a hard stop to limit the degree of rotation allowed by the posterior portion 96. The amount of rotation allowed can be tailored for the condition of the specific patient. For example, in addition to simple limits on the amount of rotation allowed, the amount of allowed rotation left may be different than the amount of allowed rotation right. That is, the allowed degree of left rotation may be greater than the allowed degree of right rotation and vice-versa.

The posterior portion 97 contains similar stop portions to those described with respect to posterior portion 96. In some embodiments, the stop portions of the posterior portion 97 are substantially identical to those of the posterior portion 96. However, in some embodiments the stop portions are different. In that regard, the stop portions of the posterior portion 97 can be tailored for the condition of the specific patient. Though not shown in the current embodiment, the posterior portions 96 and 97 may include further stop portions to limit flexion and both left and right lateral bending. Further, as described below with respect to FIGS. 6 and 7, the stop portions can increase resistance to movement in a direction rather than being a hard stop to movement in that direction.

Thus, the anterior portion 80 and the posterior portions 96 and 97 allow for movement about the same center of rotation, namely center point 88. Therefore, the anterior portion 80 will not adversely load or affect the posterior portions 96 and 97 during movement, and vice-versa. Thus, the anterior portion 80 and posterior portions 46 and 47 of the apparatus 78 function together to provide load-bearing support and preserve vertebral motion between the vertebrae 12 and 14 without adversely affecting one another.

Figure 6:
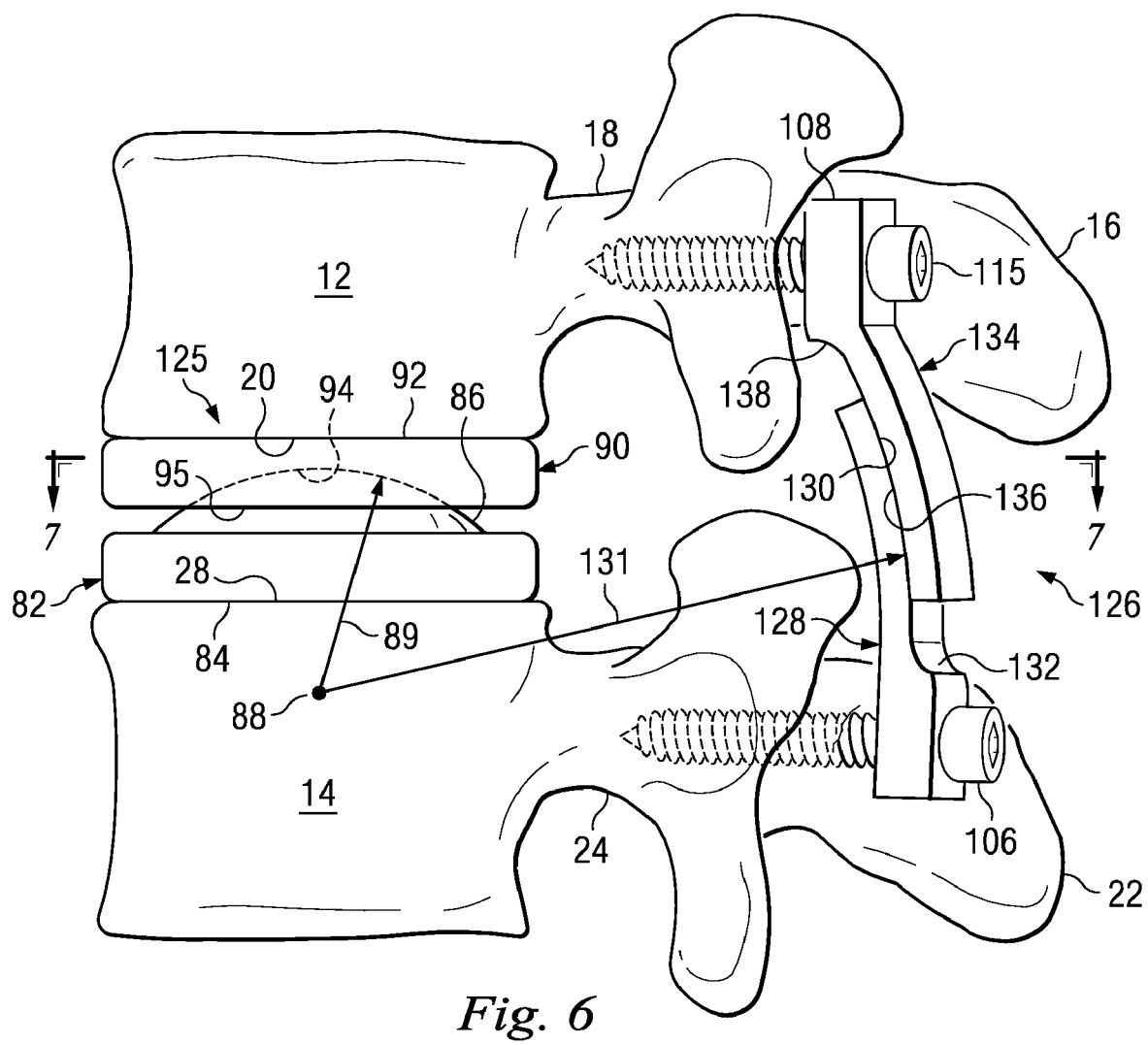
FIG. 6 is a diagrammatic side view similar to FIGS. 1 and 4, but showing an alternative embodiment.
Figure 7:
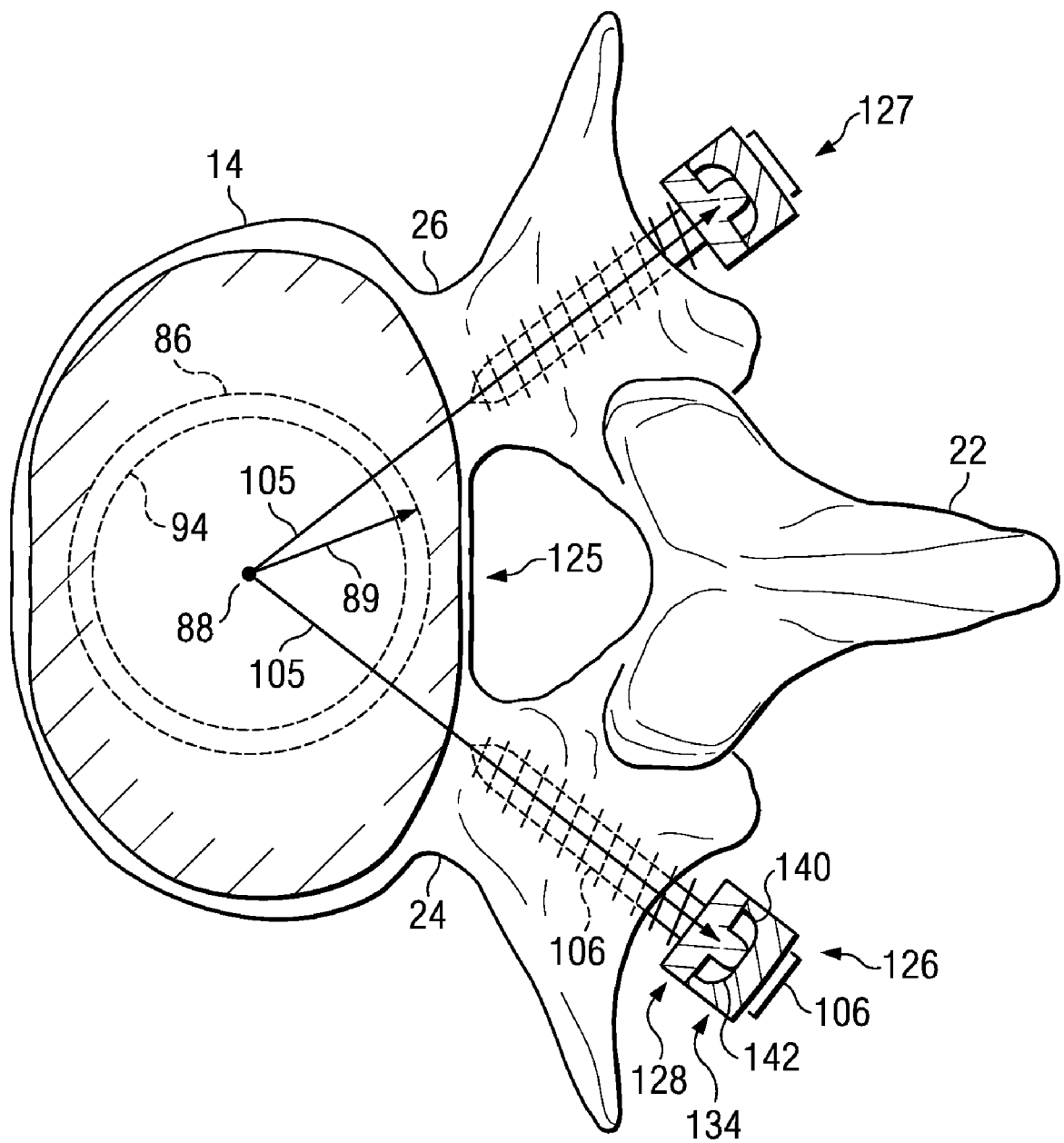
FIG. 7 is a sectional view of the arrangement of FIG. 6 taken along section line 7-7.

FIG. 6 is a diagrammatic side view similar to FIG. 4, but showing an apparatus 125 that is an alternative embodiment of the apparatus 78 described above. Apparatus 125 is similar to apparatus 78 in many respects and, therefore, many aspects will not be described in great detail. FIG. 7 is a sectional view of FIG. 6 taken along section line 7-7.

The apparatus 125 also includes two posterior portions 126 and 127. The posterior portion 127 is only presented in a partial, sectional view in FIG. 7. In the current embodiment, the posterior portion 127 is substantially similar to posterior portion 126 and, therefore, will not be described in detail. The posterior portion 126 includes an inferior part 128. The inferior part 128 includes a surface 130 that extends along the posterior side of the inferior part. As shown, the surface 130 is curved to substantially coincide with a virtual sphere centered about center point 88 with a radius 131. A stop portion 132 extends posteriorly from the inferior part 128 adjacent the surface 130. The stop portion 132 is curved to limit the range of motion allowed by the posterior portion 126.

The posterior portion 126 also includes a superior part 134. The superior part 134 includes a surface 136 that extends along the anterior side of the superior part. The surface 136 is curved to movably mate with the surface 130 of the inferior part 128. Similar to the surface 130, the surface 136 is curved to substantially coincide with the virtual sphere centered about center point 88 with radius 131. A stop portion 138 extends anteriorly from the superior part 134 adjacent surface 136. The stop portion 138 is curved and serves with stop portion 132 to limit the range of motion allowed by the posterior portion 126.

The surfaces 130 and 136 movably mate to allow for spherical, rotational movement about the center point 88. However, the degree of spherical, rotational movement allowed in extension is limited by stop portions 132 and 138. As the motion segment moves further into extension, the upper section of the inferior part 128 moves closer and closer to the stop portion 138 until they make contact. At the same time, the lower section of superior part 134 moves closer and closer to the stop portion 132 until they make contact. In the current embodiment, the stop portions 132 and 138 are positioned such that they will be contacted simultaneously by the superior part 134 and the inferior part 128, respectively. In alternative embodiments, the stop portions 132 and 138 may be staggered such that one is contacted prior to the other.

Unlike the hard stops 114, 122, and 124 described above, the stop portions 132 and 138 are gradual. That is, the curved surfaces of the stop portions 132 and 138 provide a gradual increase in resistance to movement in a direction towards further extension. The further into extension the patient moves, the more resistance the stop portions 132 and 138 create. The degree of slope of the curved surfaces of the stop portions 132 and 138 determines the amount of resistance at different degrees of extension. Again the resistance and amount of extension allowed can be tailored for the condition of the specific patient.

Further, as best seen in FIG. 7, the superior part 134 includes stop portions 140 and 142. Similar to the stop portions 132 and 138 described above, the stop portions 140 and 142 are gradual stops. The curved surfaces of the stop portions 140 and 142 provide a gradual increase in resistance to movement in a direction towards further rotation. As the motion segment rotates left or right, the inferior part 128 moves closer and closer to the stop portions 140 (in left rotation) and 142 (in right rotation) until they make contact. Once in contact, the stop portions 122 and 124 serve to increase resistance to further rotation. The further into a left or right rotational position the patient moves, the more resistance the stop portions 132 and 138 create. Again, the degree of slope of the curved surfaces of the stop portions 132 and 138 determines the amount of resistance at different degrees of extension. The resistance and amount of extension allowed can be tailored for the condition of the specific patient.

The posterior portion 127 contains similar stop portions to those described with respect to posterior portion 126. In some embodiments, the stop portions of the posterior portion 127 are substantially identical to those of the posterior portion 126. In other embodiments the stop portions are different. Though not shown in the current embodiment, the posterior portions 126 and 127 may include further stop portions to limit flexion and both left and right lateral bending. Further, the posterior portion 126 may include hard stops in addition to the gradual stops to provide an ultimate limit on the amount of allowed extension, rotation, flexion, and lateral bending.

The various components of the anterior and posterior portions of the embodiments described above may be formed of any suitable biocompatible material including metals such as cobalt-chromium alloys, titanium alloys, nickel titanium alloys, or stainless steel alloys. Ceramic materials such as aluminum oxide or alumina, zirconium oxide or zirconia, compact of particulate diamond, or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); or cross-linked UHMWPE. Further, the components may each be formed of different materials, permitting metal on metal, metal on ceramic, metal on polymer, ceramic on ceramic, ceramic on polymer, or polymer on polymer constructions. Further, the articulating surfaces described above may be treated to limit friction and resulting wear debris caused by rotational movement.

In addition to spherical, rotational movement about a center point, the anterior and posterior portions of the apparatus may be configured for additional movement patterns without adversely affecting one another. For example and without limitation, in some embodiments the anterior and posterior portions may be adapted for corresponding helical movement, translational movement, circular movement, and combinations thereof. Further, the precise motion profile for the apparatus may be determined by monitoring the 3-D motion of a motion segment. Once the 3-D motion has been measured, a corresponding motion profile for the apparatus can be determined. The anterior and posterior portions of the apparatus can then be designed to match the specific motion profile of the motion segment. In this manner, the apparatus can be tailored to the precise motion profile of the motion segment without having the anterior and posterior portions work against each other.

The anterior and posterior portions can also include features to facilitate alignment of the portions about the common center of rotation. For example, in one embodiment the anterior portion includes fiducial markers. In one aspect, the anterior portion is inserted into the disc space and the fiducial markers are visualized using fluoroscopy, CT scan, ultrasound, or other imaging techniques to determine the center of rotation for the anterior portion of the device. The fiducial markers may include any type of marker capable of indicating the center of rotation including, but not limited to, radiopaque markers (e.g., tantalum beads), RFID tags, and other known markers. The position of the anterior portion can be adjusted to align the center of rotation with a predetermined desired point of rotation. In some embodiments, the center of rotation of the anterior portion may be determined without the use of fiducial markers. For example, the center of rotation may be determined based upon the shape of the anterior portion itself.

Once the anterior portion has been positioned and its center of rotation determined, the posterior portion can be inserted and positioned to align its center of rotation with that of the anterior portion. In one embodiment, the known shape of the posterior portion is used as a guide for aligning the centers of rotation. In another embodiment, the posterior portion includes fiducial markers that can be visualized to determine its center of rotation and align it with the center of rotation of the anterior portion. In another embodiment, the posterior portion is inserted prior to the anterior portion and the anterior portion is positioned so as to align the centers of rotation of the two portions.

Other modifications of the present disclosure would be apparent to one skilled in the art. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. A method of implanting a spinal stabilization system into a vertebral motion segment having a superior vertebra and an inferior vertebra, the method comprising:
providing a spinal stabilization system, the spinal stabilization system having an anterior portion and separate first and second posterior portions; the anterior portion having an upper component and a lower component capable of spherical relative movement about an anterior center of rotation, each of the first and second posterior portions having an upper rod portion with an elongated upper articulation surface that is curved along its length and width and a lower rod portion with an elongated lower articulation surface that is curved along its length and width, the elongated upper and lower articulation surfaces articulatingly mating such that the upper and lower rod portions are capable of spherical relative movement about a posterior center of rotation defined by the elongated upper and lower articulation surfaces;
inserting the anterior portion into an anterior section of the vertebral motion segment such that the upper component engages the superior vertebra, the lower component engages the inferior vertebra, and the upper and lower components undergo spherical relative movement about a first point defined by the anterior center of rotation;
identifying the location of the first point relative to the vertebral motion segment;
inserting the first posterior portion into a first posterior section of the vertebral motion segment such that the posterior center of rotation of the first posterior portion is aligned with the first point and such that the elongated upper and lower articulation surfaces of the first posterior portion are a first distance from the first point;
fixedly securing the upper rod portion of the first posterior portion to the superior vertebra and fixedly securing the lower rod portion of the first posterior portion to the inferior vertebra such that the posterior center of rotation of the first posterior portion is maintained in alignment with the first point and such that the elongated upper and lower articulation surfaces of the first posterior portion are maintained at the first distance from the first point;
inserting the second posterior portion into a second posterior section of the vertebral motion segment such that the posterior center of rotation of the second posterior portion is aligned with the first point and such that the elongated upper and lower articulation surfaces of the second posterior portion are a second distance from the first point, the second distance being greater than the first distance; and
fixedly securing the upper rod portion of the second posterior portion to the superior vertebra and fixedly securing the lower rod portion of the second posterior portion to the inferior vertebra such that the posterior center of rotation of the second posterior portion is maintained in alignment with the first point and such that the elongated upper and lower articulation surfaces of the second posterior portion are maintained at the second distance from the first point.

2. The method of claim 1, wherein fixedly securing the upper rod portion of the first posterior portion to the superior vertebra comprises engaging a first upper fixation mechanism with a portion of the superior vertebra.

3. The method of claim 2, wherein the first upper fixation mechanism is positioned through an opening in the upper rod portion of the first posterior portion.

4. The method of claim 2, wherein fixedly securing the lower rod portion of the first posterior portion to the inferior vertebra comprises engaging a first lower fixation mechanism with a portion of the inferior vertebra.

5. The method of claim 4, wherein the first lower fixation mechanism is positioned through an opening in the lower rod portion of the first posterior portion.

6. The method of claim 4, wherein the first upper mechanism is engaged with a pedicle of the superior vertebra and the first lower mechanism is engaged with a pedicle of the inferior vertebra.

7. The method of claim 1, wherein the upper rod portion of the first posterior portion includes a first upper stop for limiting relative movement between the upper and lower rod portions of the first posterior portion.

8. The method of claim 7, wherein the first upper stop comprises a surface Bounding an upper end of the elongated upper articulation surface of the upper rod portion of the first posterior portion.

9. The method of claim 8, wherein the first upper stop comprises a substantially planar surface such that the first upper stop is a hard stop.

10. The method of claim 8, wherein the first upper stop comprises a curved surface such that the first upper stop provides a gradual increase in resistance to relative movement between the upper and lower rod portions as the lower rod portion engages the first upper stop.

11. The method of claim 10, wherein the lower rod portion of the first posterior portion includes a first lower stop for limiting relative movement between the upper and lower rod portions, the first lower stop comprising a curved surface such that the first lower stop provides a gradual increase in resistance to relative movement between the upper and lower rod portions as the upper rod portion engages the first lower stop.

12. The method of claim 11, wherein the first upper stop and the first lower stop are positioned such that the lower rod portion will contact the first upper stop simultaneously with the upper rod portion contacting the first lower stop.

13. The method of claim 7, wherein the first upper stop comprises a pair of lateral surfaces defined by a recess in the upper rod portion.

14. The method of claim 13, wherein the lower rod portion includes a projection received within the recess in the upper rod portion such that engagement of the projection with either of the pair of lateral surfaces limits the relative movement between the upper and lower rod portions.

15. The method of claim 14, wherein at least one of the pair of lateral surfaces comprises a substantially planar surface such that the at least one of the pair of lateral surfaces provides a hard stop.

16. The method of claim 14, wherein at least one of the pair of lateral surfaces comprises a curved surface such that the at least one of the pair of lateral surfaces provides a gradual increase in resistance to relative movement between the first upper and lower portions as the projection engages the at least one of the pair of lateral surfaces.

17. The method of claim 1, wherein the anterior portion includes at least one fiducial marker, and wherein the at least one fiducial marker is utilized to identify the location of the first point relative to the vertebral motion segment.

18. The method of claim 1, wherein the anterior portion is inserted into a disc space of the vertebral motion segment.

19. A method of implanting a spinal stabilization system into a vertebral motion segment having a superior vertebra and an inferior vertebra, the method comprising: inserting an anterior portion of a spinal stabilization system into an anterior section of the vertebral motion segment such that an upper component of the anterior portion engages the superior vertebra, a lower component of the anterior portion engages the inferior vertebra, and the upper and lower components undergo spherical relative movement about an anterior point of rotation defined by the anterior portion of the spinal stabilization system; fixedly securing a first posterior portion of the spinal stabilization system to a first posterior section of the vertebral motion segment such that a first posterior center of rotation of the first posterior portion is aligned with the anterior point of rotation and such that elongated upper and lower articulation surfaces of the first posterior portion articulatingly mate at a first distance from the anterior point of rotation such that the upper and lower articulation surfaces undergo spherical relative movement about the anterior point of rotation; fixedly securing a second posterior portion of the spinal stabilization system to a second posterior section of the vertebral motion segment such that a second posterior center of rotation of the second posterior portion is aligned with the anterior point of rotation and such that elongated upper and lower articulation surfaces of the second posterior portion articulatingly mate at a second distance from the anterior point of rotation such that the upper and lower articulation surfaces undergo spherical relative movement about the anterior point of rotation, wherein the second distance is greater than the first distance.

20. The method of claim 19, wherein the anterior section of the vertebral motion segment is a disc space.

21. The method of claim 20, wherein the first posterior section includes a pedicle.

22. The method of claim 19, wherein the anterior portion includes at least one fiducial marker, and wherein the at least one fiducial marker is utilized to identify a location of the anterior point of rotation relative to the vertebral motion segment.

23. The method of claim 22, wherein the location of the anterior point of rotation relative to the vertebral motion segment as identified using the at least one fiducial marker is utilized to align at least one of the first and second posterior portions of the spinal stabilization system with the anterior portion.

24. The method of claim 19, wherein fixedly securing the first posterior portion to the first posterior section comprises engaging a first upper fixation mechanism with a first posterior portion of the superior vertebra and a first lower fixation mechanism with a first posterior portion of the inferior vertebra.

25. The method of claim 24, wherein the first posterior portion of the superior vertebra is a pedicle of the superior vertebra and the first posterior portion of the inferior vertebra is a pedicle of the inferior vertebra.

26. The method of claim 25, wherein fixedly securing the second posterior portion to the second posterior section comprises engaging a second upper fixation mechanism with a second posterior portion of the superior vertebra and a second lower fixation mechanism with a second posterior portion of the inferior vertebra.

27. The method of claim 26, wherein the second posterior portion of the superior vertebra is a pedicle of the superior vertebra and the second posterior portion of the inferior vertebra is a pedicle of the inferior vertebra.

* * * * *